(12) United States Patent
Anapliotis et al.

(10) Patent No.: US 8,496,711 B2
(45) Date of Patent: Jul. 30, 2013

(54) KNEE ARTHRODESIS IMPLANT

(75) Inventors: Emmanuel Anapliotis, Berlin (DE); Curt Kranz, Berlin (DE); Martin Hilse, Berlin (DE); Guenter Lob, Munich (DE)

(73) Assignee: Merete Medical GmbH, Berlin (DE)

( * ) Notice: Subject to any disclaimer, the term of this patent is extended or adjusted under 35 U.S.C. 154(b) by 21 days.

(21) Appl. No.: 13/061,415

(22) PCT Filed: Aug. 27, 2009

(86) PCT No.: PCT/DE2009/001194
§ 371 (c)(1),
(2), (4) Date: Feb. 28, 2011

(87) PCT Pub. No.: WO2010/025704
PCT Pub. Date: Mar. 11, 2010

(65) Prior Publication Data
US 2011/0208315 A1    Aug. 25, 2011

(30) Foreign Application Priority Data

Sep. 2, 2008  (DE) .......................... 10 2008 045 291

(51) Int. Cl.
*A61F 2/38*    (2006.01)
(52) U.S. Cl.
USPC ................... 623/20.15; 623/20.21; 623/16.11
(58) Field of Classification Search
USPC ...................................... 606/62–68
See application file for complete search history.

(56) References Cited

U.S. PATENT DOCUMENTS

| | | |
|---|---|---|
| 3,987,499 A | 10/1976 | Scharbach et al. |
| 4,578,081 A | 3/1986 | Harder et al. |

(Continued)

FOREIGN PATENT DOCUMENTS

| | | |
|---|---|---|
| DE | 33 40 767 A1 | 5/1985 |
| DE | 83 06 663 U1 | 7/1986 |

(Continued)

OTHER PUBLICATIONS

International Search Report for parent application PCT/DE2009/001194, having a mailing date of Jan. 11, 2010.

(Continued)

*Primary Examiner* — Thomas J Sweet
*Assistant Examiner* — Megan Wolf
(74) *Attorney, Agent, or Firm* — Andrus, Sceales, Starke & Sawall, LLP

(57) ABSTRACT

A knee arthrodesis implant has a femur nail inserted in the bone marrow canal of the femur, and a tibia nail inserted in the bone marrow canal of the tibia, the nails being rigidly connected to each other by a connecting means. The problem of providing a knee arthrodesis implant having increased modularity as the result of increased length variability, having a reduced number of parts, and allowing simplified modification is addressed. The problem is addressed in that the connecting means has at least one collar-like module lying in the axis direction defined by the nail, the module having at least two half-shells which are connected to each other in a detachable manner and which are separated in the axis direction (LA) of the module, said half-shells together forming a passage which extends axially and through which a nail neck is inserted, and which have recesses corresponding to each other for receiving a tensioning means, said recesses being arranged coaxially in the longitudinal direction of the module and positioned perpendicular to the axis (LA). The tensioning means fixes the respective nail neck in the passage when in the tensioned state in the manner of a clamping jaw, exclusively by means of a friction fit producing a sufficient clamping torque to prevent axial displacement and rotation.

11 Claims, 7 Drawing Sheets

U.S. PATENT DOCUMENTS

Figure 1:
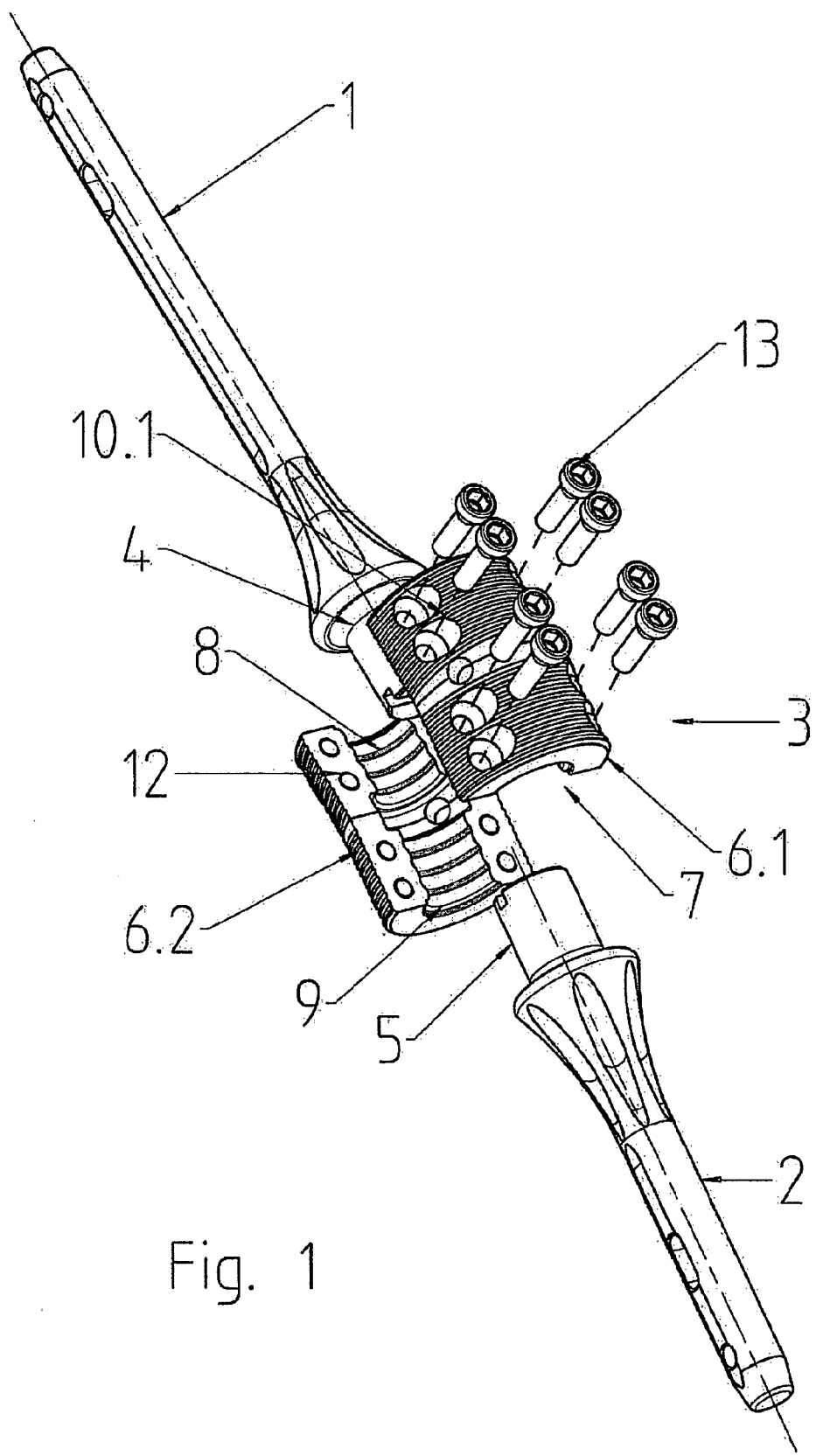

| | | | |
|---|---|---|---|
| 4,657,550 | A | 4/1987 | Daher |
| 4,790,852 | A | 12/1988 | Noiles |
| 4,846,839 | A | 7/1989 | Noiles |
| 4,938,768 | A | 7/1990 | Wu |
| 5,032,130 | A | 7/1991 | Schelhas et al. |
| 5,352,227 | A | 10/1994 | O'Hara |
| 5,626,580 | A | 5/1997 | Brosnahan |
| 5,658,349 | A | 8/1997 | Brooks et al. |
| 5,906,644 | A | 5/1999 | Powell |
| 6,217,620 | B1 | 4/2001 | Park |
| 6,238,436 | B1 | 5/2001 | Lob et al. |
| 6,264,699 | B1 | 7/2001 | Noiles et al. |
| 6,299,648 | B1 | 10/2001 | Doubler et al. |
| 6,355,068 | B1 | 3/2002 | Doubler et al. |
| 6,428,578 | B2 | 8/2002 | White |
| 6,440,171 | B1 | 8/2002 | Doubler et al. |
| 6,454,810 | B1 * | 9/2002 | Lob ............... 623/23.47 |
| 6,613,092 | B1 | 9/2003 | Kana et al. |
| 6,669,728 | B2 | 12/2003 | Despres et al. |
| 6,682,568 | B2 | 1/2004 | Despres et al. |
| 6,692,530 | B2 | 2/2004 | Doubler et al. |
| 6,699,293 | B2 | 3/2004 | White |
| 6,706,072 | B2 | 3/2004 | Dwyer et al. |
| 6,706,073 | B2 | 3/2004 | Draenert et al. |
| 6,786,932 | B1 | 9/2004 | Blackmore |
| 6,833,007 | B2 | 12/2004 | Lob |
| 6,866,683 | B2 | 3/2005 | Gerbec et al. |
| 7,435,263 | B2 | 10/2008 | Barnett et al. |
| 7,776,098 | B2 | 8/2010 | Murphy |
| 7,998,218 | B1 | 8/2011 | Brown |
| 8,100,982 | B2 | 1/2012 | Heck et al. |
| 2004/0024469 | A1 | 2/2004 | Ferree |
| 2004/0199259 | A1 | 10/2004 | Pichon et al. |
| 2005/0004679 | A1 | 1/2005 | Sederholm et al. |
| 2005/0071014 | A1 | 3/2005 | Barnett et al. |
| 2009/0171463 | A1 * | 7/2009 | Brehm .............. 623/20.14 |
| 2010/0241239 | A1 | 9/2010 | Smith |

FOREIGN PATENT DOCUMENTS

| | | |
|---|---|---|
| DE | 89 03 850 U1 | 6/1989 |
| DE | 196 33 865 A1 | 2/1998 |
| DE | 197 22 389 A1 | 12/1998 |
| DE | 20 2004 015578 U1 | 12/2004 |
| EP | 1 004 283 B1 | 5/2005 |
| EP | 1 529 493 A1 | 5/2005 |
| EP | 1 529 493 B1 | 6/2007 |
| FR | 2 670 108 A1 | 6/1992 |

OTHER PUBLICATIONS

International Search Report for parent application PCT/DE2009/001272, having a mailing date of Feb. 10, 2010.

* cited by examiner

KNEE ARTHRODESIS IMPLANT

CROSS-REFERENCE TO RELATED APPLICATIONS

This application is the U.S. national stage application of International Application No. PCT/DE2009/001194, filed Aug. 27, 2009, which International application was published on Mar. 11, 2010 as International Publication No. WO 2010/025704 A1 in the German language and which application is incorporated herein by reference. The International application claims priority of German Patent Application No. 10 2008 045 291.2, filed Sept. 2, 2008, which application is incorporated herein by reference.

The invention relates to a knee arthrodesis implant having a femur nail inserted in the bone marrow canal of the femur and a tibia nail inserted in the bone marrow canal of the tibia, and wherein the nails are rigidly connected to each other by a connecting means.

A so-called implantable orthesis for knee arthrodesis is known from EP 1 529 493 B1 comprising a femur implant having a femoral shaft that is adapted in such a way that it can be inserted in the bone marrow canal of the femoral bone and a tibia implant having a tibial shaft that is adapted in such a way that it can be inserted in the bone marrow canal of the tibia, and wherein the femur implant comprises a proximal fastening end that is adapted in such a way that it can act in conjunction with a proximal fastening end associated with the tibia implant in such a way that a rigid connection of the two implants relative to each other results, and wherein it becomes possible to implement a continuous bone reconstruction between the tibia and the femur bones and around the proximal fastening bones.

This known prior art has the disadvantage that only a single possibility for a screwed connection is envisioned in the femoral anchoring head for the purpose of fastening the femoral shaft in place, which is intended to secure the shaft against undesired axial displacement. Furthermore, it is disadvantageous that the femoral anchoring head that is disposed on the tibial anchoring head is only secured by a single truncated cone-type screw that produces a press fit between the femoral and tibial anchoring heads. This type of press fit is only difficult to achieve under surgical conditions.

It is also disadvantageous that the known orthesis comprises a relative multitude of parts therefore requiring a correspondingly large distance between the bone fragments that are to be connected with each other, thus resulting in an undesired extension of soft tissue, muscle and ligament parts complete with the corresponding traumatizing effect. Moreover, modularity is rendered more difficult.

DE 197 22 389 A1 discloses a modular knee arthrodesis implant comprising a femoral stem part by which a femoral part can be coupled via a conical clamped joint and comprising a tibial stem part by which a tibial part can be coupled via a conical clamped joint, and providing that the femoral part and the tibial part can be rigidly connected to each other by a dovetail joint. A fundamental disadvantage of this known knee arthrodesis implant consists in the fact that two conical clamped joints are necessary each of which must be secured against axial displacement by, respectively, separate set screws. Moreover, even through a dovetail connection may ensure a rigid connection in the assembled state, during a revision of such a connection, for example due to loosening, material fatigue, anchoring in the bone, complications due to infection, etc., considerable problems may arise during surgery should a lateral shift of the tibial and femoral stem parts become necessary in order to be able to exchange parts. Moreover, misaligned parts require the application of large forces in order to loosen the parts, which is regularly an undesired occurrence.

DE 83 06 663 U1 discloses an implant for bridging bony defects in the area of the knee joint which provides that the femoral and tibial shafts are configured as two shaft parts that are rigidly connectable with each other, and of which the first part can be plugged onto a conical peg on the second part.

The disadvantage that all of these solutions as set forth in the prior art share is the fact that their lengths and angular positions are not adjustable, which results in considerably restricted modularity.

OBJECTIVE

In view of this prior art, the objective of the present invention envisions describing a knee arthrodesis implant that increases the modularity of the implant by increased variability regarding length while simultaneously reducing the number of parts and simplifying revision surgery.

This object is achieved with a knee arthrodesis implant of the class as described in the introduction featuring the characteristics as set forth in claim 1.

Advantageous configurations of the knee arthrodesis implant are specified in the dependent claims.

The solution according to the invention is characterized by the fact that it is able to provide a modular system that is suitable for bridging large-area bone defects that have occurred due to one or several failed knee arthrodesis implant(s) and that has an abundance of variability with a minimal number of parts.

The transfer of the physiological maximum loads, in particular forces and moments, from the femur to the tibia is especially advantageously achieved if the connecting means between the femur nail and tibia nail comprises, in the direction of the axis of the nails, at least one collar-shaped module having at least two elements that are divided in the axial direction and detachably connected with each other and that configure together an axially extending passage for inserting a nail shaft in the proximal and distal ends of the passage, and comprising recesses that correspond to each other and that are disposed coaxially in the longitudinal direction of the module, respectively perpendicular relative to the axis, for receiving a tension means, which fastens in the tensioned state the respective nail neck exclusively by a frictional closure, in the way of a clamping jaw, with sufficient torque inside the passage. This ensures that a physiological application of force into the femur and the tibia can take place.

The present invention is based on the teaching that a collar-type module that engages on the nail shaft of the femur nail and tibia nail by way of a clamping jaw can achieve a line-shaped frictional closure extending along the circumference of the nail neck between the nail neck and the passage that will securely prevent any axial displacement and/or rotational movement of the parts that constitute the connection, even when larger loads are applied. The line-type contact precludes any fretting at the contact sites by arresting any back and forth movements. The line-type acting frictional closure is achieved by a profile texture that is envisioned on the internal wall of the passage, and wherein the neck diameters of the femur nail and the tibia nail are harmonized with the inside diameter of the passage.

Using the tension means that are disposed in the longitudinal direction of the module directly adjacent relative to each other, it is possible to secure the frictional closure by applying a correspondingly high torque. A sufficiently large torque is generated when the hexagon socket head screws are screwed into the recesses, which are envisioned with corresponding internal threads, using a torque wrench.

It is furthermore especially advantageous if the clamping-type connection between the shaft of the femur nail or tibia nail and the collar-type module is easily detachable due to the module's semi-shell configuration, even during a later surgical revision, whereby the traumatizing effect on the body tissues in the area of the arthrodesis is held to a very minimum. The surgery is thereby much simplified because all tension means are ventrally accessible.

Due to the variability of the length of the module, the implant according to the invention is easily adjustable to the varied requirements by different patients. Special advantages are also achievable, in particular, if modules of different or equal lengths are connected to each other via a module connector, whereby it is possible to considerably increase the length variability of the module that connects the femur nail and the tibia nail with each other.

A preferred embodied example according to the invention envisions an angling of the module from dorsal to ventral in the caudal direction, preferably between 5 and 15°, for adjusting the extension, flexion and valgus/varus positions of the joint, thereby achieving a slightly bent position of the stiffened joint and/or varus/valgus positions of the stiffened joint.

A further preferred embodied example according to the invention provides that one of the modules has a round anchor plate for support in cases involving with large bone openings.

In another embodied example according to the invention all parts of the implant, preferably the connecting module, have a rough surface in order to improve the integrative growth properties of the implant in the surgically treated implant area.

In a further advantageous improvement of the invention the outside diameter of the nail neck is adjusted to the inside diameter of the passage in the connecting module, and wherein nails of varying lengths and shaft lengths are envisioned.

All parts of the knee arthrodesis implant according to the invention are made of a material that is well tolerated by and resistant to the body, preferably a metallic material, for example titanium, tantalum, niobium or their alloys.

Further advantages and details are disclosed in the subsequent description in reference to the enclosed drawings.

EMBODIED EXAMPLE

Figure 2:
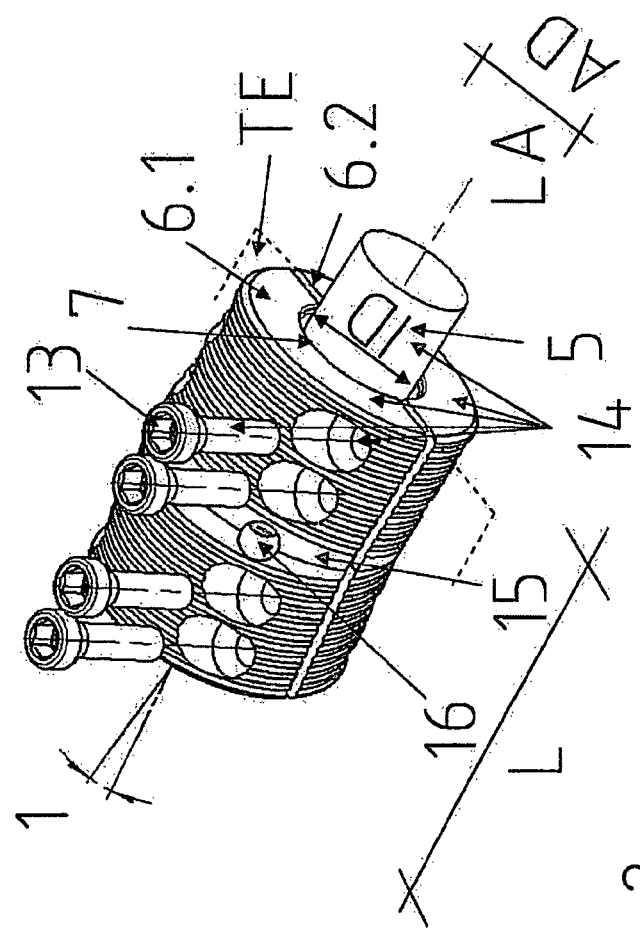
Figure 3:
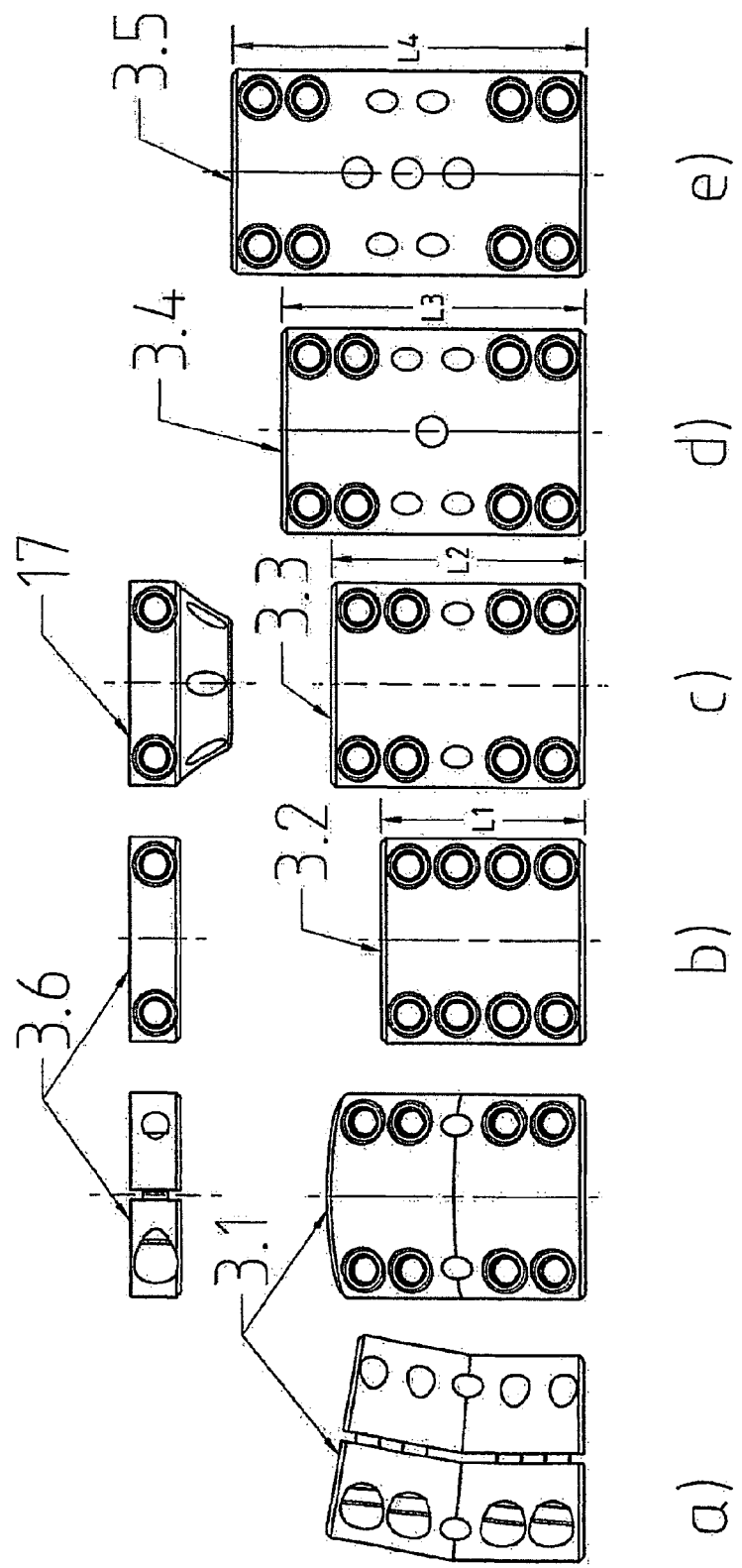
Figure 4:
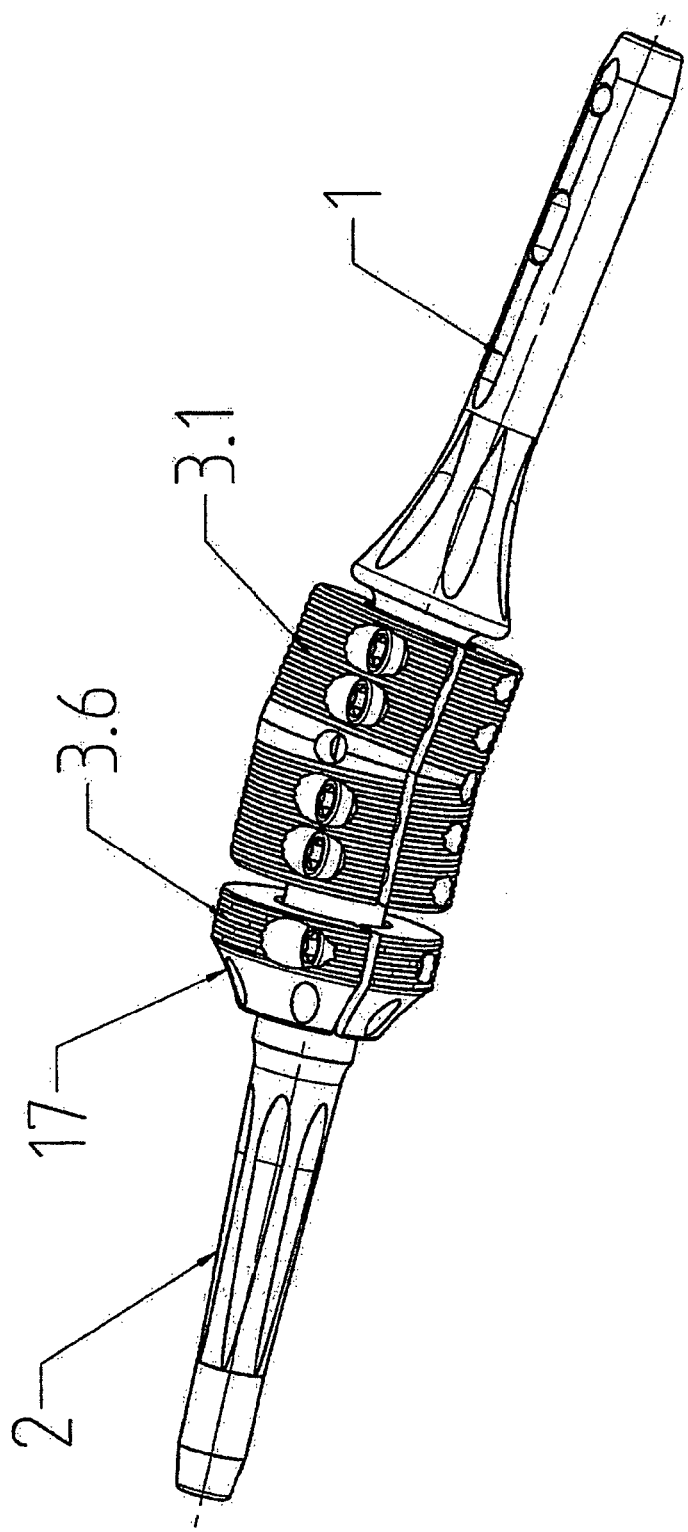
Figure 5:
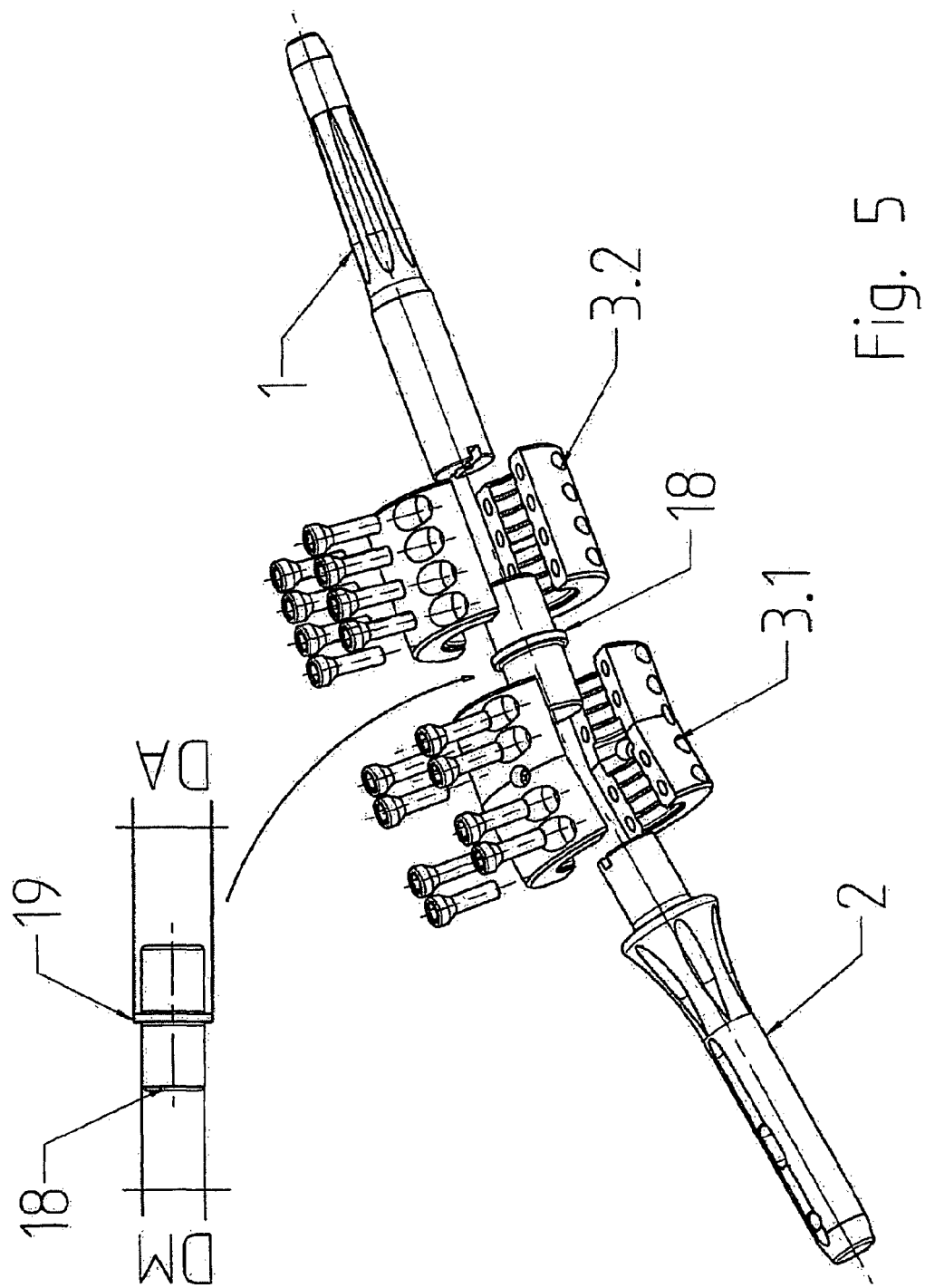
Figure 6:
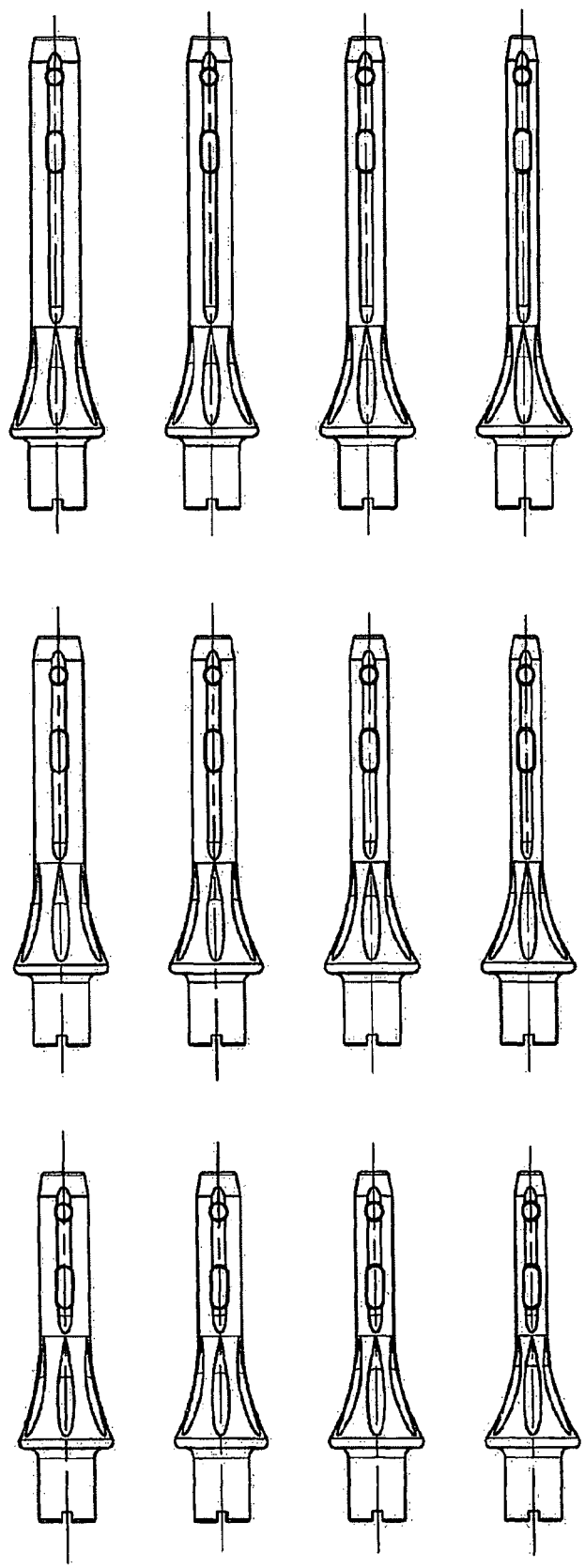
Figure 7:
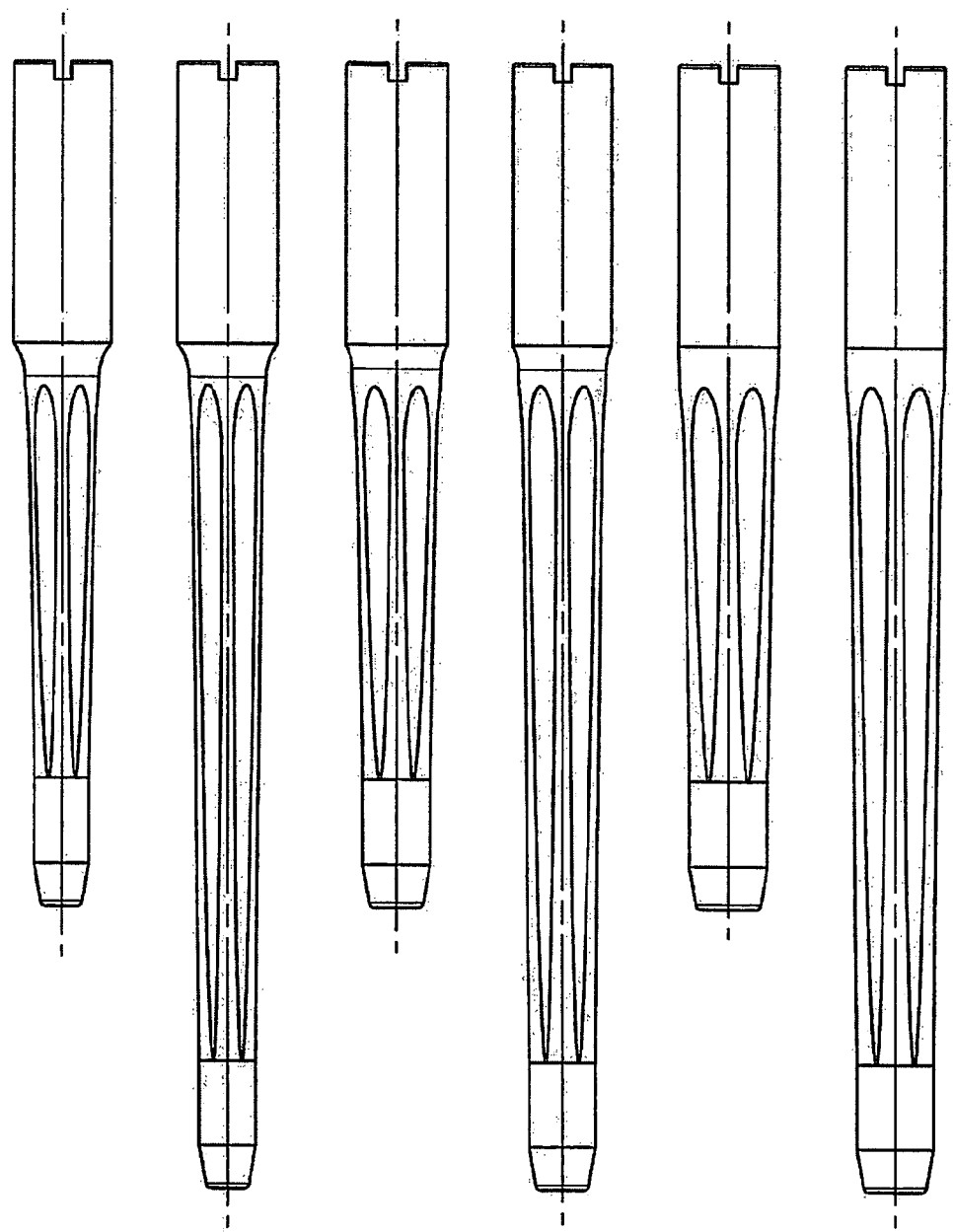

Subsequently, the invention will be illustrated in further detail using an embodied example. Shown are in:

FIG. 1 an exploded view of the knee arthrodesis implant according to the invention with an angled connecting module; in FIG. 2 a perspective view of an angled connecting module; in FIGS. 3a to 3e a top view of different connecting modules of a kit of the knee arthrodesis implant according to the invention; in FIG. 4 a perspective view of a variant of the knee arthrodesis implant according to the invention with round anchor plate; in FIG. 5 an exploded view of a further variant of the knee arthrodesis implant according to the invention with an angled connecting module and a further connecting module; in FIG. 6 a top view of arthrodesis nails with distal locking of different lengths and diameters; and in FIG. 7 a top view of arthrodesis nails without distal locking of different lengths and diameters.

FIG. 1 shows an exploded view of the basic structure of the arthrodesis implant according to the invention. The arthrodesis implant that is inserted in order to bridge large-area bony defects due to a failed primary implant surgery or a resection of the metaphyseal area of the femur and tibia is comprised of a femur nail 1, a tibia nail 2 and a connecting module 3. The femur nail 1 is inserted and anchored in the bone marrow canal of the femur, not shown here; and the tibia nail 2 is inserted and anchored in the bone marrow canal of the tibia, not shown here. The nails 1 and 2 are of different lengths and diameters; plus they are anatomically adjusted to the contours of the respective marrow canals. Locking screws and/or a star-shaped profile provide sufficient protection against rotation inside the marrow canal.

The femur nail 1 and the tibia nail 2 both have a cylindrical nail neck 4 and 5 made of solid material. The femur nail 1 is rigidly connected to the tibia nail 2 by the connecting module 3, which circumgrips the nail necks 4 and 5 respectively in a collar-type manner. The connecting module 3 consists of two parts comprising two cylindrical half-shell 6.1 and 6.2 that are configured substantially identically. Both half-shells 6.1 an 6.2 define in their assembled state a passage 7 having an inside wall 8 with a profile 9 that is disposed perpendicular relative to the longitudinal axis LA of the module. Respectively four recesses 10.1 and 10.2, arranged next to each other, are incorporated in each of the walls of the half-shell wall 11 in such a way that the recesses are arranged coaxially relative to the longitudinal axis LA of module 3 and perpendicular relative to the dividing plane TE that is virtually fixed by the half-shells 6.1 and 6.2 so that at least eight recesses are assigned to each connecting module 3. An internal thread 12 is incorporated in the recesses 10.1 of the half-shell 6.2; and a hexagon socket head screw 13 can be screwed into the recess 10.1 of the half-shell 6.1.

The half-shells 6.1 and 6.2, together with the respective hexagon socket head screw 13 and the corresponding internal thread 12, constitute a tensioning means 14 of the type of a clamping jaw, which positions itself around the cylinder-shaped nail neck 4 and/or 5 when the hexagon socket head screw 13 is tightened, creating between the profile 9 and the nail shaft 4 and/or 5 a continuous, line-type frictional closure connection along the circumference. The outside diameter AD of the nail shaft 4 and/or 5 therein is correspondingly harmonized with the inside diameter ID of the passage 7. The resistance of this frictional closure against an axial or rotational displacement of the components can be adjusted very precisely and exactly by applying a defined torque to the hexagon socket head screw 13. A secure connection is achieved between the femur nail 1 and the tibia nail 2 by assigning four tensioning means 14 respectively to nail necks 4 and 5.

All tensioning means 14 are ventrally aligned and thus easily accessible during any revision at a later time without any need for traumatizing large areas of body tissue.

The connecting module 3 has—as shown in FIG. 2—an angling 15 in order to easily achieve extension, flexion and valgus/varus positions of the joint. The angling 15 can vary widely, for example between 1 and 30°, and is provided with openings 16 that can be used to introduce inflammation-inhibiting or long-term acting antibiotics.

FIGS. 3a to 3e show different connecting modules 3.1 to 3.5 having different lengths L, such as, for example, a connecting module 3.1 with angling 15, a connecting module 3.2 without angling having one length L1, respectively, (FIG. 3a, 3b), a connecting module 3.3 having a length L2 (FIG. 3c), L3 (FIG. 3d) and a connecting module 3.4 having a length L4 (FIG. 3e).

It is understood that the connecting modules 3.3 to 3.5, respectively, can also be provided with an angling 15. Whether or not there is an angling will depend on the actual circumstances and conditions involving the respective patient.

FIG. 4 shows a knee arthrodesis implant according to the invention that is especially suited for large bone openings inside the femur. Through the connecting module 3.6 of a length L of 10 mm, a round anchor plate 17 is fastened on the nail neck of the femur nail 1 and fastened by a frictional closure, thereby making it possible to fill a large bone opening inside bone marrow canal of the femur. Function and configuration of the connecting module 3.6 having a length L of 10 mm corresponds to the description as outlined in section [0029] for the connecting modules 3.1 to 3.5.

FIG. 5 shows a knee arthrodesis implant according to the invention in which a connecting module 3.2 on the side of the femur and a connecting module 3.1 on the side of the tibia can be connected with each other by a round rod-shaped module connector 18. The module connector 18 consists of solid material the diameter DM of which is harmonized with the inside diameter ID of the passage 7. The module connector 18 has in its center a continuous stop 19 having a diameter DA that is larger in comparison to the inside diameter ID of the passage 10. The frictional closure connection between the module connector 18 and the connecting modules 3.1 and 3.2 is achieved by inserting the respective ends of the module connector 18 in the corresponding ends of the passage 7 of the connecting module 3.1 and 3.2 and by tensioning of the respectively associated tensioning means 14. This way it is possible to combine the individual connecting modules 3.1 to 3.6 with each other and achieve a large variability in terms of different lengths.

FIGS. 6 and 7 show examples of arthrodesis nails with and without distal locking having different lengths and diameters and the neck diameters AD of which are harmonized with the inside diameter ID of the passage 7 of the respective connecting modules 3.1 to 3.6.

All parts of the knee arthrodesis implant according to the invention, except for the hexagon socket head screws, are made of a metallic material that is tolerated by and resistant to the body having surfaces of a defined roughness, for example of between 20 µm and 80 µm. On the on hand, this is intended to increase the friction coefficient of the frictional closure partners as well as, on the other hand, promote integrative growth of the implant.

Configurations of the invention are not limited to the previously outlined embodied examples. Rather, variants that may deviate from the described solution are conceivable, even with implementations of a fundamentally different kind.

LIST OF THE REFERENCE SIGNS

Femur nail 1
Tibia nail 2
Connecting module 3, 3.1-3.6
Nail neck of 1 4
Nail neck of 2 5
Half shells 6.1, 6.2
Passage 7
Internal wall of 7 8
Profile 9
Recesses 10.1, 10.2
Half-shell wall 11
Internal thread 12
Hexagon socket head screw 13
Tensioning means 14
Angling 15
Openings in 15 16
Round anchor plate 17
Module connector 18
Stop 19
Outside diameter of 4, 5 AD
Outside diameter of 19 DA
Diameter of 18 DM
Inside diameter of 7 ID
Length of 3, 3.1-3.6 L
Longitudinal axis of 3, 3.1-3.6 LA

The invention claimed is:

1. A knee arthrodesis implant comprising:
a femur nail having a first end for insertion into a bone marrow canal of a femur and a second, opposite end having a femur nail neck;
a tibia nail having a first end for insertion into a bone marrow canal of a tibia and a second, opposite end having a tibia nail neck;
a collar-type module rigidly connecting the femur nail to the tibia nail, the collar-type module having two longitudinally separated half shells that when connected form a longitudinally extending passage through the collar-type module, a first end of the longitudinally extending passage receiving the femur nail neck therein and a second, opposite end of the longitudinally extending passage receiving the tibia nail neck therein;
wherein the collar-type module is angled along its length, thereby allowing the femur and tibia nails to extend from the respective first and second ends of the longitudinally extending passage at an angle from one another;
wherein the two half shells each comprise a plurality of corresponding recesses that extend through the half shells perpendicularly to the longitudinally extending passage;
wherein each recess in the plurality of recesses receives a tensioning screw, whereby tightening of the tensioning screws holds the femur and tibia nail necks within the respective first and second ends of the longitudinally extending passage by frictional contact;
wherein a resistance of the frictional contact can be adjusted by application of a certain torque to the tensioning screws, thereby controlling axial displacement and radial rotation of the collar-type module with respect to the femur and tibia nail necks, thereby allowing for gradual adjustment of extension, flexion and valgus and varus positions of a knee joint as the collar-type module is rotated to adjust the angle at which the femur and tibia nails extend from one another;
wherein the collar-type module comprises first and second collar-type modules; and
further comprising a module connector configured to connect the first and second collar-type modules by insertion of a first end of the module connector into a longitudinally extending passage of the first collar-type module and insertion of a second, opposite end of the module connector into a longitudinally extending passage of the second collar-type module and tightening of tensioning screws in a plurality of recesses in each of the first and second collar-type modules.

2. The knee arthrodesis implant of claim 1, wherein the module connector comprises a cylindrical rod with a continuous stop extending radially outwardly from an outer surface of the rod, one side of the continuous stop abutting the first collar-type module, and an opposite side of the continuous stop abutting the second collar-type module.

3. The knee arthrodesis implant of claim 1, wherein the first and second ends of the module connector are held in the respective longitudinally extending passages of the first and second collar-type modules exclusively by frictional contact, and wherein a resistance of the frictional contact can be adjusted by application of a predefined torque to the tensioning screws, thereby controlling axial displacement and radial rotation of the collar-type modules with respect to the first and second ends of the module connector.

4. The knee arthrodesis implant of claim 1, wherein both of the first and second collar-type modules are angled along their respective lengths.

5. The knee arthrodesis implant of claim 1, wherein at least one of the first and second collar-type modules is not angled along its length.

6. The knee arthrodesis implant of claim 1, further comprising a profile on an inner wall of the longitudinally extending passage, wherein the frictional contact occurs between the profile and the femur and tibia nail necks.

7. The knee arthrodesis implant of claim 6, wherein the profile extends radially within the inner wall of the longitudinally extending passage.

8. The knee arthrodesis implant of claim 6, wherein the profile extends diagonally within the inner wall of the longitudinally extending passage.

9. A knee arthrodesis implant comprising:
a femur nail having a first end for insertion into a bone marrow canal of a femur and a second, opposite end having a femur nail neck;
a tibia nail having a first end for insertion into a bone marrow canal of a tibia and a second, opposite end having a tibia nail neck;
a collar-type module rigidly connecting the femur nail to the tibia nail, the collar-type module having two longitudinally separated half shells that when connected form a longitudinally extending passage through the collar-type module, a first end of the longitudinally extending passage receiving the femur nail neck therein and a second opposite end of the longitudinally extending passage receiving the tibia nail neck therein;
wherein the collar-type module is angled along its length, thereby allowing the femur and tibia nails to extend from the respective first and second ends of the longitudinally extending passage at an angle from one another;
wherein the two half shells each comprise a plurality of corresponding recesses that extend through the half shells perpendicularly to the longitudinally extending passage;
wherein each recess in the plurality of recesses receives a tensioning screw, whereby tightening of the tensioning screws holds the femur and tibia nail necks within the respective first and second ends of the longitudinally extending passage by frictional contact;
wherein a resistance of the frictional contact can be adjusted by application of a certain torque to the tensioning screws, thereby controlling axial displacement and radial rotation of the collar-type module with respect to the femur and tibia nail necks, thereby allowing for gradual adjustment of extension, flexion and valgus and varus positions of a knee joint as the collar-type module is rotated to adjust the angle at Which the femur and tibia nails extend from one another;
wherein the collar-type module comprises first and second collar-type modules; and
wherein a length of the first collar-type module differs from a length of the second collar-type module.

10. The knee arthrodesis implant of claim 9, wherein a diameter of the first collar-type module differs from a diameter of the second collar-type module.

11. A knee arthrodesis implant comprising:
a femur nail having a first end for insertion into a bone marrow canal of a femur and a second, opposite end having a femur nail neck;
a tibia nail having a first end for insertion into a bone marrow canal of a tibia and a second, opposite end having a tibia nail neck;
a collar-type module rigidly connecting the fermur nail to the tibia nail, the collar-type module having two longitudinally separated half shells that when connected form a longitudinally extending passage through the collar-type module, a first end of the longitudinally extending passage receiving the femur nail neck therein and a second, opposite end of the longitudinally extending passage receiving the tibia nail neck therein;
wherein the collar-type module is angled along its length, thereby allowing the femur and tibia nails to extend from the respective first and second ends of the longitudinally extending passage at an angle from one another;
wherein the two half shells each comprise a plurality of corresponding recesses that extend through the half shells perpendicularly to the longitudinally extending passage;
wherein each recess in the plurality of recesses receives a tensioning screw, whereby tightening of the tensioning screws holds the femur and tibia nail necks within the respective first and second ends of the longitudinally extending passage by frictional contact;
wherein a resistance of the frictional contact can be adjusted by application of a certain torque to the tensioning screws, thereby controlling axial displacement and radial rotation of the collar-type module with respect to the femur and tibia nail necks, thereby allowing for gradual adjustment of extension, flexion, and valgus and varus positions of a knee joint as the collar-type module is rotated to adjust the angle at which the femur and tibia nails extend from one another;
further comprising a round anchor plate adjacent an end of the collar-type module; and
further comprising a module connector for connecting the collar-type module to the round anchor plate by insertion of a first end of the module connector into the longitudinally extending passage of the collar-type module and insertion of a second, opposite end of the module connector into a longitudinally extending passage of the round anchor plate.

* * * * *